United States Patent
Sogabe

(10) Patent No.: US 9,707,926 B2
(45) Date of Patent: Jul. 18, 2017

(54) EMERGENCY REPORTING SYSTEM

(71) Applicant: DENSO CORPORATION, Kariya, Aichi-pref. (JP)

(72) Inventor: Haruhiko Sogabe, Kariya (JP)

(73) Assignee: DENSO CORPORATION, Kariya, Aichi-pref. (JP)

( * ) Notice: Subject to any disclaimer, the term of this patent is extended or adjusted under 35 U.S.C. 154(b) by 0 days.

(21) Appl. No.: 14/893,449

(22) PCT Filed: May 20, 2014

(86) PCT No.: PCT/JP2014/002633
§ 371 (c)(1),
(2) Date: Nov. 23, 2015

(87) PCT Pub. No.: WO2014/192247
PCT Pub. Date: Dec. 4, 2014

(65) Prior Publication Data
US 2016/0107609 A1     Apr. 21, 2016

(30) Foreign Application Priority Data

May 29, 2013   (JP) .................................. 2013-113145

(51) Int. Cl.
*B60Q 1/00*      (2006.01)
*B60R 22/48*     (2006.01)
(Continued)

(52) U.S. Cl.
CPC ............ *B60R 22/48* (2013.01); *A61B 5/6893* (2013.01); *A61B 5/7282* (2013.01); *G08B 25/00* (2013.01);
(Continued)

(58) Field of Classification Search
CPC .................................................. B60R 22/48
(Continued)

(56) References Cited

U.S. PATENT DOCUMENTS 6,204,757 B1 *   3/2001  Evans ..................... B60R 22/48
                                                     340/436
6,431,872 B1 *   8/2002  Shiraishi ................. G09B 9/05
                                                     273/442

(Continued)

FOREIGN PATENT DOCUMENTS

JP       2002127857 A    5/2002
JP       2004148998 A    5/2004
JP          4357084 B2   11/2009

OTHER PUBLICATIONS

International Search Report and Written Opinion (in Japanese with English Translation) for PCT/JP2014/002633, mailed Jul. 29, 2014; ISA/JP.

*Primary Examiner* — Santiago Garcia
(74) *Attorney, Agent, or Firm* — Harness, Dickey & Pierce, P.L.C.

(57) ABSTRACT

An emergency reporting system includes a seat belt detection unit, a speed change detection unit, an injury determination unit, and an emergency reporting unit. The seat belt detection unit detects a fastening state of seat belt when the vehicle stops moving assisted by collision prevention process that prevents vehicle collision in advance. The speed change detection unit detects a speed change during a time interval from when the collision prevention process is performed to when the vehicle is stopped. The injury determination unit determines the injury level of the vehicle occupant based on the detection results of the seat belt detection unit and the speed change detection unit. The emergency reporting unit emergently reports determined injury level of the vehicle occupant to a prescribed reporting destination. The emergency reporting system can properly determine the injury level of the vehicle occupant when vehicle collision is prevented in advance, and can emergently report the determined injury level.

7 Claims, 2 Drawing Sheets

(51) Int. Cl.
  *G08B 25/01*  (2006.01)
  *G08B 25/00*  (2006.01)
  *G08B 25/10*  (2006.01)
  *A61B 5/00*  (2006.01)
  *G08G 1/00*  (2006.01)

(52) U.S. Cl.
  CPC ........... *G08B 25/016* (2013.01); *G08B 25/10* (2013.01); *B60R 2022/4816* (2013.01); *G08G 1/205* (2013.01)

(58) Field of Classification Search
  USPC ........................................................ 340/436
  See application file for complete search history.

(56) References Cited

U.S. PATENT DOCUMENTS

| | | | |
|---|---|---|---|
| 6,728,616 B1* | 4/2004 | Tabe | B60R 21/017 180/268 |
| 2001/0011810 A1* | 8/2001 | Saiguchi | B60N 2/4221 280/728.1 |
| 2003/0030264 A1* | 2/2003 | Motozawa | B60R 22/1952 280/806 |
| 2004/0017073 A1* | 1/2004 | Pavlov | B60N 2/002 280/806 |
| 2004/0055806 A1* | 3/2004 | Masuda | B60N 2/4279 180/282 |
| 2004/0122573 A1 | 6/2004 | Mizutani | |
| 2004/0169411 A1* | 9/2004 | Murray | B60R 22/105 297/486 |
| 2006/0033615 A1* | 2/2006 | Nou | G08B 13/19647 340/539.13 |
| 2006/0119091 A1* | 6/2006 | Takao | B60R 22/022 280/801.1 |
| 2006/0226648 A1* | 10/2006 | Cuddihy | B60R 21/0132 280/806 |
| 2007/0096447 A1* | 5/2007 | Tabe | B60R 21/017 280/735 |
| 2008/0275616 A1* | 11/2008 | Houten | B60R 22/48 701/70 |
| 2010/0007191 A1* | 1/2010 | Takao | B60R 22/02 297/475 |
| 2011/0093165 A1* | 4/2011 | Miller | B60R 22/48 701/36 |
| 2013/0088001 A1* | 4/2013 | Park | B60R 22/03 280/801.2 |
| 2013/0088057 A1* | 4/2013 | Szakelyhidi | B60N 2/2806 297/250.1 |
| 2013/0175845 A1* | 7/2013 | Yoshioka | B60R 22/36 297/476 |
| 2014/0103696 A1* | 4/2014 | Odate | B60R 22/03 297/469 |
| 2014/0188347 A1* | 7/2014 | Tabe | B60R 21/0152 701/45 |
| 2014/0343788 A1* | 11/2014 | Hosey | F02D 29/02 701/36 |
| 2016/0001781 A1* | 1/2016 | Fung | G06F 19/345 701/36 |

* cited by examiner

EMERGENCY REPORTING SYSTEM

CROSS REFERENCE TO RELATED APPLICATIONS

This application is a U.S. National Phase Application under 35 U.S.C. 371 of International Application No. PCT/JP2014/002633 filed on May 20, 2014 and published in Japanese as WO 2014/192247 A1 on Dec. 4, 2014. This application is based on and claims the benefit of priority from Japanese Patent Application No. 2013-113145 filed on May 29, 2013. The entire disclosures of all of the above applications are incorporated herein by reference.

TECHNICAL FIELD

The present disclosure relates to an emergency reporting system that determines an injury level of a vehicle occupant and reports the injury level to a prescribed reporting destination as an emergency.

BACKGROUND ART

An emergency reporting system mounted in a vehicle is conventionally known. An emergency reporting system disclosed, for instance, in Patent Literature 1 determines, based on the manipulation of a reporting switch and a collision detected by a collision detection unit, whether the emergency state of a vehicle occupant is "severe" or "mild," and reports the emergency state to a prescribed reporting destination. Herein, the collision detection unit is a device which detects a collision of a vehicle.

Only when a collision is detected by the collision detection unit, the emergency reporting system disclosed in Patent Literature 1 determines that the emergency state of a vehicle occupant is "severe." However, even when no vehicle collision occurs, the emergency state of a vehicle occupant may be "severe" on the basis, for instance, of whether the seat belt is fastened on the vehicle occupant and of a speed change before the stoppage of the vehicle. In other words, conventional emergency reporting systems are not capable of properly determining the emergency state of a vehicle occupant when no vehicle collision occurs. This may cause an over triage or under triage, and accordingly, an appropriate medical procedure may fail to be provided to a vehicle occupant corresponding to an emergency state of the vehicle occupant.

PRIOR ART LITERATURES

Patent Literature

Patent Literature 1: JP 4357084 B2

SUMMARY OF INVENTION

In view of the foregoing difficulties, it is an object of the present disclosure to provide an emergency reporting system that is capable of properly determining an injury level of a vehicle occupant when a vehicle collision is prevented before a collision outbreak and emergently reporting the determined injury level.

According to an aspect of the present disclosure, an emergency reporting system includes a seat belt detection unit, a speed change detection unit, an injury determination unit, and an emergency reporting unit. The seat belt detection unit detects whether a seat belt is fastened on an occupant of a vehicle when the vehicle performs a collision prevention process and then stops moving for avoiding an occurrence of a collision. The collision prevention process is a process performed by the vehicle to prevent the occurrence of the collision. The speed change detection unit detects a speed change of the vehicle during a time interval from a time at which the collision prevention process is performed to a time at which the vehicle stops moving. The injury determination unit determines an injury level of the occupant of the vehicle based on detection results detected by the seat belt detection unit and the speed change detection unit. The emergency reporting unit reports the determined injury level of the occupant of the vehicle to a prescribed reporting destination.

The above emergency reporting system makes it possible to properly determine an injury level of a vehicle occupant when a vehicle collision is prevented in advance and emergently report the determined injury level.

BRIEF DESCRIPTION OF DRAWINGS

The above and other objects, features, and advantages of the present disclosure will become more apparent from the following detailed description made with reference to the accompanying drawings. In the drawings.

EMBODIMENTS FOR CARRYING OUT INVENTION

First Embodiment

An embodiment of the present disclosure will now be described with reference to the accompanying drawings.

Figure 1:
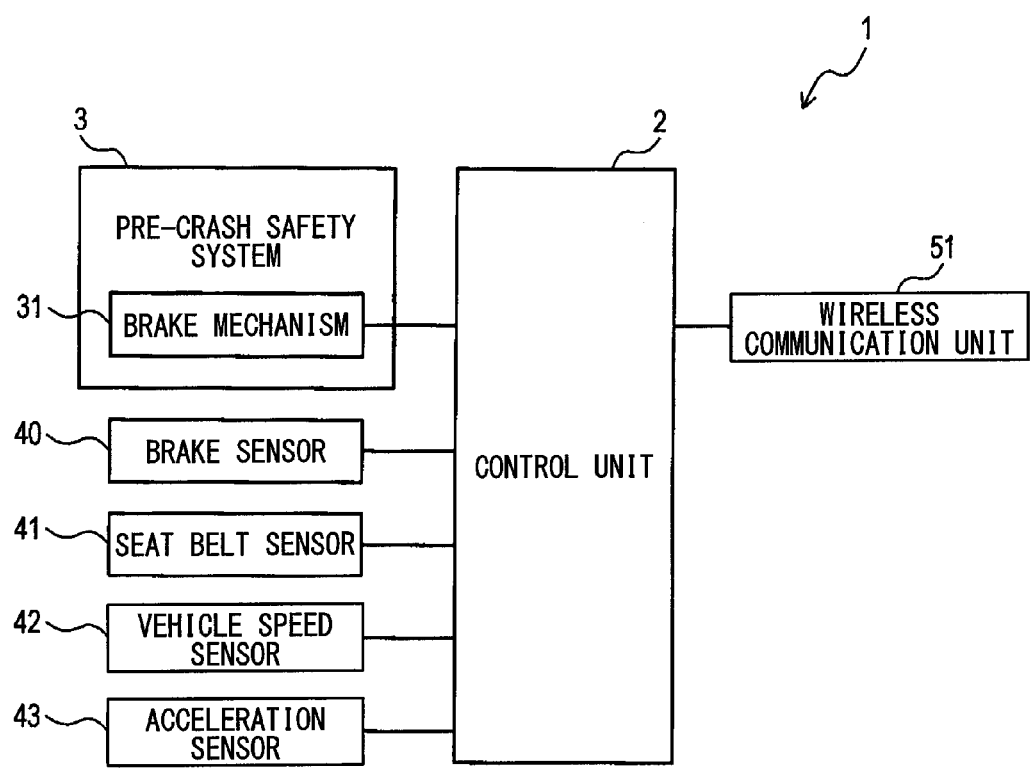
FIG. 1 is a diagram illustrating a configuration of an emergency reporting system according to a first embodiment of the present disclosure.

As shown in FIG. 1, an emergency reporting system 1 according to the present embodiment includes a control unit 2, a pre-crash safety system 3, a brake sensor 40, a seat belt sensor 41, a vehicle speed sensor 42, an acceleration sensor 43, and a wireless communication unit 51.

The pre-crash safety system 3 is equipped to a vehicle and used to predict and prevent a collision of the vehicle in advance. Specifically, the pre-crash safety system 3 includes a pre-crash sensor (not shown), a brake mechanism 31 of the vehicle, a brake control device (not shown), and a pre-crash control unit (not shown). The pre-crash sensor predicts a vehicle collision. The brake control device controls the brake mechanism 31. The pre-crash control unit controls the brake control device.

The pre-crash sensor may be provided mainly by a millimeter-wave radar that transmits and receives radar waves to detect a target such as a preceding vehicle and acquires target information including the location and speed of the target and the location and speed of a host vehicle. The pre-crash sensor outputs the acquired target information to the pre-crash control unit.

The pre-crash sensor may also be provided mainly by a vehicle-mounted camera and a radar device. In this case, the camera positioned to capture an image showing a view in the traveling direction of the host vehicle and acquire the target information based on the captured image. The pre-crash sensor may also be provided mainly by a radar device. In this case, the radar device transmits and receives laser lights to detect the target such as a preceding vehicle and acquire the target information. Alternatively, the pre-crash sensor may be provided a combination of the aforementioned millimeter-wave radar, a vehicle-mounted camera, or a laser radar device.

The pre-crash control unit is mainly provided by a microcomputer that includes a CPU, a ROM, and a RAM. The pre-crash control unit determines the probability of a vehicle collision on the basis of an output from the pre-crash sensor, and controls the brake control device on the basis of the result of determination.

The brake sensor 40 detects an operation (automatic braking) of the brake mechanism 31 that is performed by the pre-crash control unit. When the brake sensor 40 detects automatic braking, that is, the activation of the pre-crash safety system 3, the brake sensor 40 outputs relevant information to the control unit 2.

The seat belt sensor 41 detects whether a seat belt is fastened on a vehicle occupant, and outputs the result of detection to the control unit 2.

The vehicle speed sensor 42 detects the traveling speed of the vehicle. More specifically, the vehicle speed sensor 42 detects a change in the speed of the vehicle. The vehicle speed sensor 42 detects a vehicle speed change in the front-rear, left-right, and up-down directions of the vehicle and outputs the results of detection to the control unit 2.

The acceleration sensor 43 detects the acceleration of the vehicle. More specifically, the acceleration sensor 43 detects an impact (the magnitude of impact) applied to the vehicle. The acceleration sensor 43 detects the acceleration (the magnitude of impact) in the front-rear, left-right, and up-down directions of the vehicle, and outputs the results of detection to the control unit 2. Further, the acceleration sensor 43 may be used as an auxiliary device that assists the vehicle speed sensor 42 in detecting a vehicle speed change.

The control unit 2 is mainly provided by a microcomputer that includes a CPU, a ROM, and a RAM. The control unit 2 receives information from the brake sensor 40, the seat belt sensor 41, the vehicle speed sensor 42, and the acceleration sensor 43. The control unit 2 determines the injury level of a vehicle occupant on the basis of such input information and causes the wireless communication unit 51 to emergently report the determined injury level of the vehicle occupant to an emergency report center (not shown).

The wireless communication unit 51 wirelessly communicates with the emergency report center through a wide area communication network. More specifically, the injury level of a vehicle occupant, which is determined by the control unit 2, is output to the wireless communication unit 51. The wireless communication unit 51 then transmits information about the vehicle occupant's injury level, which is output from the control unit 2 and input to the wireless communication unit 51, and information about, for example, the location of the vehicle to the emergency report center through the wide area communication network. For instance, on the basis of the injury level of the vehicle occupant, the emergency report center selects an emergency response team who is to be dispatched to an incident site and a medical institution that performs a medical procedure, and conveys relevant information as needed.

Figure 2:
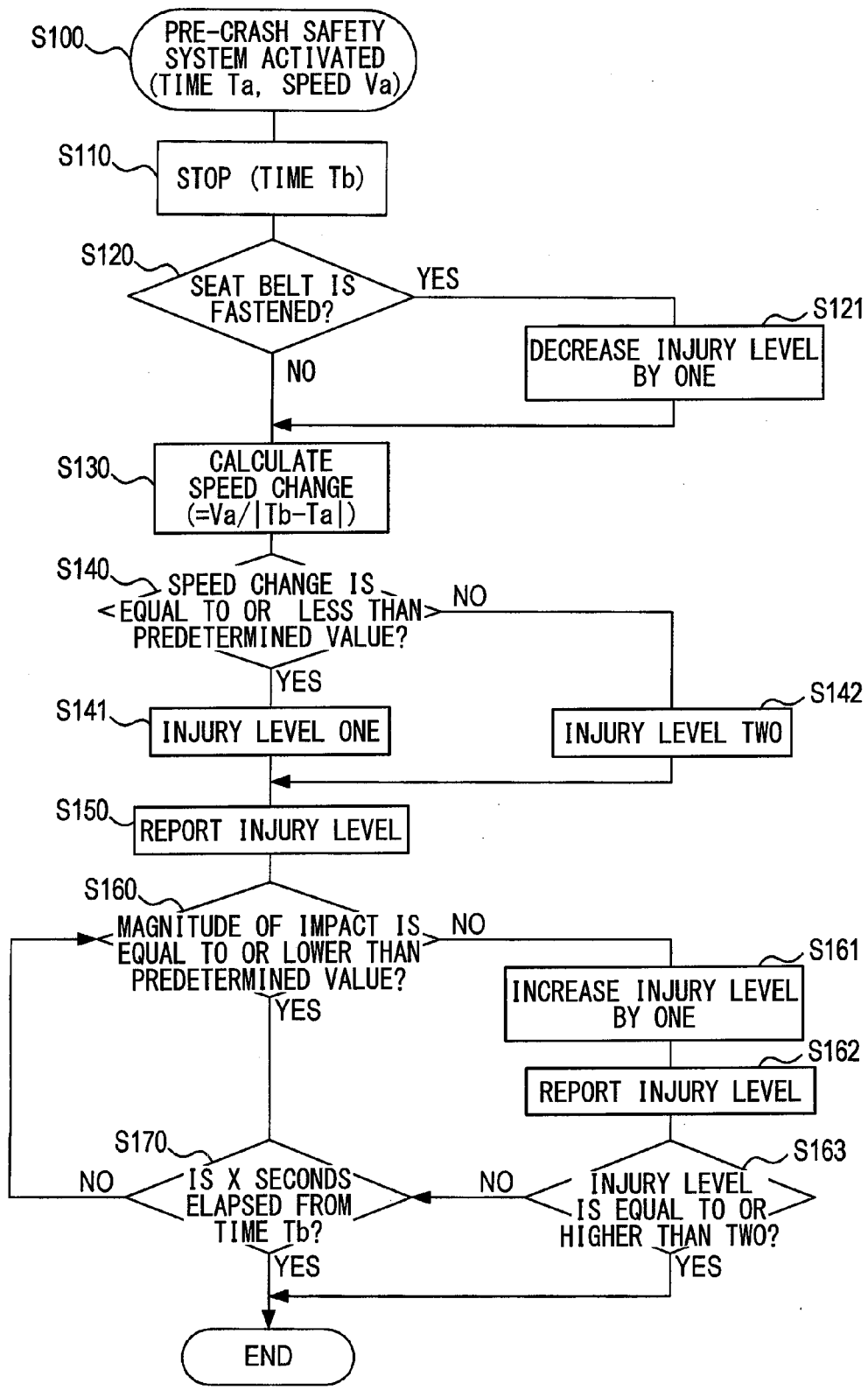
FIG. 2 is a flowchart illustrating an emergency reporting process performed in the first embodiment.

The following will describe a process performed by the control unit 2 to make an emergency report with reference to the flowchart of FIG. 2.

The process starts when the pre-crash safety system 3 is activated (S100). More specifically, the process starts when the brake sensor 40 detects automatic braking by the pre-crash control unit and relevant information is input to the control unit 2. It is assumed that the information relevant to the automatic braking is input to the control unit 2 at a time Ta, and the vehicle has a speed Va at the time Ta. Subsequently, the vehicle is stopped due to automatic braking by the pre-crash safety system 3 (S110). As a result, a vehicle collision is prevented. It is assumed that the vehicle stops travelling at a time Tb.

When the pre-crash safety system 3 is activated and causes the vehicle to stop travelling, the control unit determines whether a seat belt is fastened on a vehicle occupant based on the detection result of the seat belt sensor 41 (S120). When the control unit 2 determines that the seat belt is fastened on the vehicle occupant, the numerical value indicative of an injury level is decreased by one from a later-determined injury level (S121). When the control unit determines that the seat belt is not fastened on the vehicle occupant, the control unit 2 proceeds to S130 without executing S121.

Next, the control unit 2 calculates a vehicle speed change during the time interval from the time at which the pre-crash safety system 3 is activated to the time at which the vehicle is stopped by automatic braking based on the detection result of the vehicle speed sensor 42 (S130). More specifically, the vehicle speed change is calculated using an expression speed change=Va/|Tb−Ta|. At this time, vehicle speed changes in the front-rear, left-right, and up-down directions of the vehicle are calculated.

Next, the control unit 2 determines whether each vehicle speed change is equal to or less than a predetermined value (S140). Specifically, the control unit 2 determines whether each of the vehicle speed changes in the front-rear, left-right, and up-down directions of the vehicle is equal to or less than a corresponding predetermined value. When the vehicle speed changes in all the directions are equal to or less than the corresponding predetermined values, the control unit 2 determines the injury level as level 1 (S141). When the vehicle speed change in a certain direction is greater than the corresponding predetermined value, the control unit 2 determines the injury level as level 2 (S142).

Next, the control unit 2 controls the wireless communication unit 51 to emergently report the determined injury level to the emergency report center (S150). When the seat belt is fastened (process proceeds to S121), the numerical value indicative of the injury level determined in S141 or S142 is decreased by one and reported to the emergency report center.

Next, after the host vehicle is stopped by the automatic braking of the pre-crash safety system 3, when the acceleration sensor 43 detects an impact applied to the vehicle due to, for example, a collision with another vehicle, the control unit 2 determines whether the magnitude of the impact is equal to or lower than a predetermined value (S160). Specifically, the control unit determines whether each of the magnitudes of the impact in the front-rear, left-right, and up-down directions of the vehicle is equal to or less than a corresponding predetermined value.

When the magnitudes of the impact in all the directions are equal to or less than the corresponding predetermined values, the control unit 2 determines whether X seconds have been elapsed from the time Tb. When X seconds have not elapsed from the time Tb, process returns to S160. When X seconds have been elapsed from the time Tb, the control unit 2 ends the process.

When the magnitude of the impact in a certain direction is greater than the predetermined value, the control unit 2 increases the numerical value indicative of the injury level reported in S150 by one (S161) and then controls the wireless communication unit 51 to report the emergency level to the report center again (S162). Then, the control unit 2 determines whether the reported injury level is equal to or higher than level 2 (S163). When the injury level is lower than 2, the process proceeds to S170. When the injury level is equal to or higher than level 2, the control unit 2 ends the process.

In the present embodiment, the process performed by the pre-crash safety system 3 corresponds to a collision prevention process; the seat belt sensor 41 corresponds to a seat belt detection unit; the vehicle speed sensor 42 corresponds to a speed change detection unit; the acceleration sensor 43 corresponds to an impact detection unit; steps S120, S140, and S160, which are performed by the control unit 2, correspond to an injury determination unit; and steps S150 and S162 correspond to an emergency reporting unit. Further, the brake sensor 40 corresponds to a collision prevention detection unit.

The following will describe advantages of the emergency reporting system 1 according to the present embodiment.

When the pre-crash safety system 3 is activated, the emergency reporting system 1 according to the present embodiment controls the control unit 2 to determine the injury level of a vehicle occupant on the basis of the detection result detected by the seat belt sensor 41 and the vehicle speed sensor 42. In other words, when the pre-crash safety system 3 predicts a vehicle collision and prevents the vehicle collision in advance, the emergency reporting system 1 detects whether the seat belt is fastened on the vehicle occupant and detects a vehicle speed change before vehicle stoppage, and determines the injury level of the vehicle occupant on the basis of the detection result.

With above-described configuration, the injury level of a vehicle occupant can be properly determined when a vehicle collision is predicted and prevented. The determined injury level of the vehicle occupant is then emergently reported to the emergency report center. Thus, an appropriate medical procedure can be performed on the basis of the injury level of the vehicle occupant. This makes it possible to avoid overtriage and undertriage.

In the emergency reporting system 1 according to the present embodiment, the vehicle speed sensor 42 detects a vehicle speed change in the front-rear, left-right, and up-down directions of the vehicle. This makes it possible to more accurately detect a vehicle speed change during the time interval from the time at which the pre-crash safety system 3 is activated to the time at which the vehicle stops moving. Thus, the injury level of the vehicle occupant can be determined at a higher accuracy.

The emergency reporting system 1 further includes the acceleration sensor 43 that detects an impact applied to the vehicle. If the acceleration sensor 43 detects an impact applied to the vehicle during the time interval from the time (Tb) at which the vehicle is stopped by the operation of the pre-crash safety system 3 to a time at which a predetermined period of time (X seconds) has elapsed since the stoppage of the vehicle, the control unit 2 determines again the injury level of the vehicle occupant on the basis of the result of detection by the acceleration sensor 43 and emergently rereports the redetermined injury level of the vehicle occupant.

In other words, even if the pre-crash safety system 3 is activated to prevent a vehicle collision, an accident may be followed by the activation of the pre-crash safety system 3. For example, another vehicle may collide with the host vehicle after the host vehicle is stopped. Therefore, when the acceleration sensor 43 detects an impact applied to the host vehicle during the time interval from the time (Tb) at which the vehicle is stopped to a time at which the predetermined period of time (X seconds) has elapsed since the stoppage of the vehicle, the injury level of the vehicle occupant is redetermined on the basis of the result of detection by the acceleration sensor 43, and the re-determined injury level is reported to outside. As described above, the injury level of a vehicle occupant are determined in two separate stages and information related to the injury level of the vehicle occupant is emergently transmitted to the emergency report center.

The acceleration sensor 43 detects the magnitudes of impact applied in the front-rear, left-right, and up-down directions of the vehicle. Therefore, the impact applied to the vehicle can be more accurately detected. This makes it possible to determine the injury level of a vehicle occupant with a higher accuracy.

As described above, the present embodiment provides the emergency reporting system 1 that is capable of properly determining the injury level of a vehicle occupant when a vehicle collision is prevented in advance, and emergently reporting the determined injury level.

The present disclosure is not limited to the first embodiment, which has been described above. It will be obvious to those skilled in the art that various changes may be made without departing from the scope of the present disclosure.

In the first embodiment, the collision prevention process is performed to exercise brake control (automatic braking) by activating the pre-crash safety system 3. Alternatively, the collision prevention process may be performed by allowing a vehicle occupant to exercise brake control. More specifically, the collision prevention process may be performed by allowing a vehicle occupant to depress a brake to an excessive extent, thereby generating excessive deceleration. Such an excessive braking operation can be detected by the brake sensor 40 included in the first embodiment.

The emergency reporting system 1 according to the first embodiment is a system confined within a vehicle. Alternatively, the emergency reporting system 1 may be configured so that a part of process is performed outside the vehicle. For example, data indicative of the results of detection, for instance, by the brake sensor 40, the seat belt sensor 41, the vehicle speed sensor 42, and the acceleration sensor 43 may be transmitted to a server installed outside the vehicle, and the server may be configured to determine the injury level of a vehicle occupant and emergently report the determined injury level to an emergency report center.

The speed change detection unit (the vehicle speed sensor 42) detects the vehicle speed change in each direction of the vehicle. Thus, an origin of a vehicle occupant's injury (the location of the injury) can be estimated to a certain extent. When information about such an estimated origin of the vehicle occupant's injury is emergently reported together with the injury level, a more appropriate medical procedure and preparation can be performed for the vehicle occupant.

Suppose that the vehicle speed change in the front-rear direction of the vehicle is equal to or greater than the predetermined value. In this case, it can be estimated that a chest of the vehicle occupant might be severely hit. Suppose that the vehicle speed change in the left-right direction of the vehicle is equal to or greater than the predetermined value. In this case, it can be estimated that a temporal region of the vehicle occupant might be severely hit. Suppose that the vehicle speed change in the up-down direction of the vehicle is equal to or greater than the predetermined value. In this case, it can be estimated that a parietal region of the vehicle occupant might be severely hit.

The impact detection unit (the acceleration sensor 43) detects the magnitude of impact (the amount of impact) applied in each direction of the vehicle. Thus, an origin of a vehicle occupant's injury (the location of the injury) can be estimated to a certain extent. When information about such an estimated origin of the vehicle occupant's injury is emergently reported together with the injury level, a more appropriate medical procedure and preparation can be performed for the vehicle occupant.

Suppose that the amount of impact applied in the front-rear direction of the vehicle is equal to or greater than the predetermined value. In this case, it can be estimated that a chest of the vehicle occupant might be severely hit. Suppose that the amount of impact applied in the left-right direction of the vehicle is equal to or greater than the predetermined value. In this case, it can be estimated that a temporal region of the vehicle occupant might be severely hit. Suppose that the amount of impact applied in the up-down direction of the vehicle is equal to or greater than the predetermined value. In this case, it can be estimated that a parietal region of the vehicle occupant might be severely hit.

The present disclosure includes the following aspects.

The emergency reporting system 1 according to the present disclosure includes the seat belt detection unit 41, the speed change detection unit 42, and the control unit 2. The seat belt detection unit 41 detects whether a seat belt is fastened on an occupant of a vehicle when the vehicle performs a collision prevention process and then stops moving for avoiding an occurrence of a collision. The speed change detection unit 42 detects a change in the speed of the vehicle during the time interval from the time at which the collision prevention process is performed to the time at which the vehicle stops moving. The control unit 2 determines the injury level of the vehicle occupant on the basis of whether the seat belt is fastened or not and of the vehicle speed change, and emergently reports the injury level of the vehicle occupant to a prescribed reporting destination. The control unit 2 functions as the injury determination unit. The control unit 2 also functions as the emergency reporting unit. The injury determination unit determines the injury level of the vehicle occupant on the basis of whether the seat belt is fastened on the vehicle occupant and of the vehicle speed change. The emergency reporting unit emergently reports the injury level of the vehicle occupant, which is determined by the injury determination unit, to the prescribed reporting destination.

When the collision prevention process is performed, the emergency reporting system determines the injury level of the vehicle occupant on the basis of the detection results detected by the seat belt detection unit 41 and the speed change detection unit 42. In other words, when a vehicle collision is prevented by performing the collision prevention process, the injury level of the vehicle occupant is determined on the basis of the detection results of a seat belt fastening state and a vehicle speed change before the stoppage of the vehicle.

With the above-described configuration, the injury level of the vehicle occupant can be properly determined when a vehicle collision is prevented in advance by the collision prevention process. The determined injury level of the vehicle occupant is then emergently reported to the emergency report center by the emergency reporting unit. Thus, an appropriate medical procedure can be performed on the basis of the injury level of the vehicle occupant. This makes it possible to avoid overtriage and undertriage.

As described above, the present disclosure provides an emergency reporting system that is capable of properly determining the injury level of a vehicle occupant when a vehicle collision is prevented in advance by the collision prevention process, and emergently reporting the determined injury level.

In the above emergency reporting system 1, the speed change detection unit 42 may alternatively be configured to be able to detect a vehicle speed change in at least one of the front-rear, the left-right direction, or the up-down direction of the vehicle. When such an alternative configuration is employed, a vehicle speed change during the time interval from the time at which the collision prevention process is performed to the time at which the vehicle stops moving can be detected with a higher accuracy. Thus, the injury level of a vehicle occupant can be determined with a higher accuracy.

When the speed change detection unit 42 detects a vehicle speed change in various directions of the vehicle, the origin of a vehicle occupant's injury (the location of the injury) can be estimated to a certain extent. When information about such an estimated origin of the vehicle occupant's injury is emergently reported together with the injury level, a more appropriate medical procedure can be performed for the vehicle occupant.

For example, when a vehicle speed change in the front-rear direction of the vehicle is equal to or greater than a predetermined value, it can be estimated that the chest of a vehicle occupant might be severely hit. When a vehicle speed change in the left-right direction of the vehicle is equal to or greater than the predetermined value, it can be estimated that a temporal region of the vehicle occupant might be severely hit. When a vehicle speed change in the up-down direction of the vehicle is equal to or greater than the predetermined value, it can be estimated that a parietal region of the vehicle occupant might be severely hit.

The emergency reporting system 1 may further include the impact detection unit 43. When the impact detection unit 43 detects an impact applied to a vehicle during the time interval from a time at which the vehicle stops moving by the operation of the collision prevention process to a time at which a predetermined time period has elapsed from the stoppage of the vehicle, the injury determination unit may determine again the injury level of the vehicle occupant on the basis of the detection result detected by the impact detection unit, and the emergency reporting unit may emergently report again the injury level of the vehicle occupant that is redetermined by the injury determination unit.

In other words, even when the collision prevention process is performed to prevent a vehicle collision, an accident may be caused by the collision prevention process. For example, another vehicle may collide with the host vehicle after the host vehicle stops moving. Therefore, when the impact detection unit 43 detects an impact applied to the host vehicle during the time interval from a time at which the vehicle stops moving to a time at which the predetermined period of time has elapsed from the stoppage of the vehicle, the injury level of the vehicle occupant is determined again on the basis of the result of detection by the impact detection unit 43 and emergently reported again. This makes it possible to determine the injury level of a vehicle occupant in two separate stages and emergently transmit information about the injury level of the vehicle occupant.

The impact detection unit 43 may alternatively be configured to be able to detect the magnitude of the impact applied to the vehicle in at least one of the front-rear direction, the left-right direction, or the up-down direction of the vehicle. When such an alternative configuration is employed, an impact applied to the vehicle can be detected with a higher accuracy. Thus, the injury level of a vehicle occupant can be determined with a higher accuracy.

When the impact detection unit 43 detects the magnitude of impact (the amount of impact) applied in various directions of the vehicle, the origin of the vehicle occupant's injury (the location of the injury) can be estimated to a certain extent. When information about such an estimated origin of the vehicle occupant's injury is emergently reported together with the injury level, a more appropriate medical procedure can be performed for the vehicle occupant.

For example, when the amount of impact applied in the front-rear direction of the vehicle is equal to or greater than a predetermined value, it can be estimated that the chest of a vehicle occupant might be severely hit. When the amount of impact applied in the left-right direction of the vehicle is equal to or greater than the predetermined value, it can be estimated that a temporal region of the vehicle occupant might be severely hit. When the amount of impact applied in the up-down direction of the vehicle is equal to or greater than the predetermined value, it can be estimated that a parietal region of the vehicle occupant might be severely hit.

The collision prevention process may alternatively include a process performed by the pre-crash safety system 3 equipped to the vehicle. The use of such an alternative configuration makes it possible to properly determine the injury level of a vehicle occupant when the pre-crash safety system is brought into action (activated) to prevent a vehicle collision. The pre-crash safety system may be brought into action (activated), for example, by allowing the pre-crash safety system to exercise brake control.

The collision prevention process may be performed by allowing a vehicle occupant to exercise brake control instead of permitting the aforementioned pre-crash safety system to exercise, for instance, brake control. For example, the collision prevention process may be performed by allowing the vehicle occupant to depress a brake to an excessive extent, thereby generating excessive deceleration.

The emergency reporting system 1 may further include the collision prevention detection unit that detects the execution of the collision prevention process. The use of such a configuration makes it possible to improve the accuracy of detection operations that are performed by the seat belt detection unit 41 and the speed change detection unit 42 after the execution of the collision prevention process.

While the present disclosure has been described in conjunction with the foregoing embodiment, it is to be understood that the present disclosure is not limited to the foregoing embodiment and the structure of the foregoing embodiment. The present disclosure is intended to cover various exemplary modifications and equivalent modifications. In addition, various combinations and configurations and other combinations and configurations that additionally include only one element or more than one element or include a smaller number of elements are also within the spirit and scope of the present disclosure.

The invention claimed is:

1. An emergency reporting system comprising:
    a seat belt detection unit detecting whether a seat belt is fastened on an occupant of a vehicle when the vehicle activates a collision prevention process and then stops moving for avoiding an occurrence of a collision, the collision prevention process being a process performed by the vehicle to prevent the occurrence of the collision by activating a brake;
    a speed change detection unit detecting a speed change of the vehicle during a time interval from a time at which the collision prevention process is activated to a time at which the vehicle stops moving without a collision;
    an injury determination unit determining an injury level that is a level of an injury that the occupant of the vehicle has received in a situation that the occurrence of the collision is predicted and prevented by the collision prevention process based on detection results detected by the seat belt detection unit and the speed change detection unit; and
    an emergency reporting unit reporting the determined injury level of the occupant of the vehicle to a prescribed reporting destination.

2. The emergency reporting system according to claim 1, wherein
    the speed change detection unit detects the speed change of the vehicle in at least one of a front-rear direction, a left-right direction, or an up-down direction of the vehicle.

3. The emergency reporting system according to claim 1, further comprising
    an impact detection unit detecting an impact applied to the vehicle, wherein,
    when the impact detection unit detects the impact applied to the vehicle during a time interval from the time at which the vehicle stops moving by the collision prevention process to a time at which a predetermined time period has elapsed from a stoppage of the vehicle,
    the injury determination unit determines again the injury level of the occupant of the vehicle based on a detection result detected by the impact detection unit, and
    the emergency reporting unit reports again the injury level of the occupant of the vehicle, which is re-determined by the injury determination unit.

4. The emergency reporting system according to claim 3, wherein
    the impact detection unit detects a magnitude of the impact applied to the vehicle in at least one of a front-rear direction, a left-right direction, or an up-down direction of the vehicle.

5. The emergency reporting system according to claim 1, wherein
    the vehicle is equipped with a pre-crash safety system, and
    the collision prevention process includes a process performed by the pre-crash safety system.

6. The emergency reporting system according to claim 1, further comprising:
    a wireless communication unit,
    wherein the emergency reporting unit reports the determined injury level of the occupant of the vehicle to the prescribed reporting destination outside the vehicle via the wireless communication unit.

7. The emergency reporting system according to claim 1, wherein the injury level is determined after the vehicle stops moving.

* * * * *